United States Patent
Chu et al.

(10) Patent No.: US 11,453,635 B2
(45) Date of Patent: Sep. 27, 2022

(54) METHOD OF MAKING CYCLOBUTANE-1, 2-DIACIDS DEGRADABLE BUILDING BLOCKS FOR MATERIALS

(71) Applicant: THE UNIVERSITY OF NORTH DAKOTA, Grand Forks, ND (US)

(72) Inventors: Qianli Chu, Grand Forks, ND (US); Zhihan Wang, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 0 days.

(21) Appl. No.: 17/283,873

(22) PCT Filed: Nov. 25, 2019

(86) PCT No.: PCT/US2019/062972
§ 371 (c)(1),
(2) Date: Apr. 8, 2021

(87) PCT Pub. No.: WO2020/117519
PCT Pub. Date: Jun. 11, 2020

(65) Prior Publication Data
US 2021/0347718 A1    Nov. 11, 2021

Related U.S. Application Data

(60) Provisional application No. 62/775,275, filed on Dec. 4, 2018.

(51) Int. Cl.
*C07C 51/353*    (2006.01)

(52) U.S. Cl.
CPC ............................ *C07C 51/353* (2013.01)

(58) Field of Classification Search
CPC .................................................. C07C 51/353
See application file for complete search history.

(56) References Cited

PUBLICATIONS

Amjaour et al., "Scalable preparation and property investigation of a cis-cyclobutane-1,2-dicarboxylic acid from β-trans-cinnamic acid" Chem Commun., Nov. 30, 2018, vol. 55 pp. 214-217, p. 214 col. 2, para 3; p. 215, col. 1, para 1; p. 2015, col. 1, para 4, Supplemental Materials, p. 2 para2. (Year: 2018).*
International Search Report and Written Opinion for PCT Application No. PCT/US2019/62972, dated Feb. 28, 2020, pp. 11.
Amjaour et al., "Scalable preparation and property investigation of a cis-cyclobutane-1,2-dicarboxylic acid from b-tans-cinnamic acid in Chem Commun." Nov. 30, 2018, vol. 55 pp. 214-217, p. 214 col. 2, para 3; p. 215, col. 1, para 1 p. 2015, col. 1, para 4, Supplemental Materials, p. 2 para 2.
Amjaour et al., "Scalable preparation and property investigation of a ciscyclobutane-1, 2-dicarboxylic acid from?-trans-cinnamic acid," Nov. 30, 2018.
Wang et al., "Cyclobutane-1, 3-Diacid (CBDA): A Semi-Rigid Building Block Prepared by [2+2] Photocyclization for Polymeric Material in Scientific Reports," 2017, vol. 7:13704, pp. 1-7.
Gutekunst et al., Applications of C—H Functionalization Logic to Cyclobutane Synthesis in Journal of Organic Chemistry, 2014, vol. 79, pp. 2430-2452.
International Preliminary Report on Patentability for PCT Application No. PCT/US2019/62972, dated Jun. 17, 2021, pp. 6.

* cited by examiner

*Primary Examiner* — Deborah D Carr
(74) *Attorney, Agent, or Firm* — Kinney & Lange, P. A.

(57) ABSTRACT

A method of making cyclobutane-1,2-diacid building blocks includes using trans-cinnamic acid in its beta form (head to head packing) and photodimerizing the trans-cinnamic acid to create cis-cyclobutane-1,2-dicarboxylic acid (CBDA-4).

19 Claims, 23 Drawing Sheets

CBDA-1

CBDA-2

CBDA-4

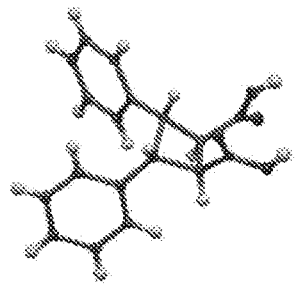 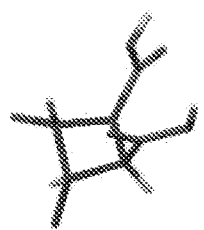 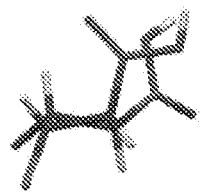
FIG. 12A　　　　FIG. 12B　　　　FIG. 12C
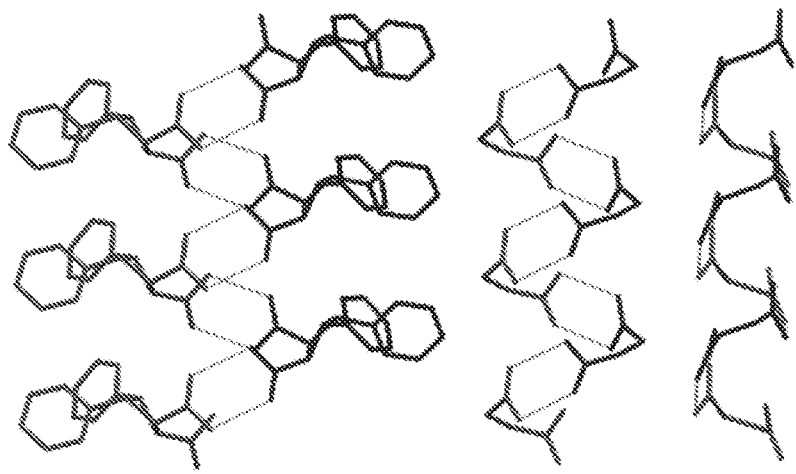
FIG. 12D Before photodimerization After photocycloaddition After Heating

METHOD OF MAKING CYCLOBUTANE-1, 2-DIACIDS DEGRADABLE BUILDING BLOCKS FOR MATERIALS

CROSS-REFERENCE TO RELATED APPLICATION(S)

This application claims the benefit of U.S. Provisional Application No. 62/775,275 filed Dec. 4, 2018 for "METHOD OF MAKING CYCLOBUTANE-1, 2-DIACIDS DEGRADABLE BUILDING BLOCKS FOR MATERIALS" by Q. Chu and Z Wang.

STATEMENT OF GOVERNMENT INTEREST

This invention was made with government support under Grant number IIA-1355466 awarded by National Science Foundation. The government has certain rights in the invention.

BACKGROUND

Synthetic polymers have a broad array of applications in industry. Building blocks for synthetic polymers must be stable molecules capable of producing polymer formations.

Diacids are widely used in modern materials. An example is the aliphatic diacid-adipic acid, used to make Nylon 66. Aromatic diacids have also found a variety of applications in materials. For instance, terephthalic acid, or benzene-1,4-dicarboxylic acid, is a chemical synthesized from a compound in crude oil. It is a building block in polyethylene terephthalate (PET), which is widely known for its use in plastic beverage bottles. Researchers are currently trying to find a biomass-based diacid to serve as an alternative to terephthalic acid. A prime candidate has been the furan-based building block 2,5-furandicarboxylic acid, which was named one of the top-12 value-added chemicals for "green" chemistry.

Dicarboxylic acids have a variety of applications in polymers, metal-organic materials, and medicine. In particular, cyclobutanedicarboxylic acids (CBDAs) and their derivatives represent promising building blocks for polymers such as thermoplastics and thermosets. In these polymers, CBDA serves as a diacid monomer or cross-linker. CBDA monomers and their derivatives can be synthesized from bio-based chemicals, such as biomass waste, and many of them are degradable.

However, certain CBDA monomers are difficult to synthesize. For instance, cis-cyclobutane-1,2-dicarboxylic acid (CBDA-4) is difficult to reliably produce in large quantities. Current processes are labor intensive and produce only a small amount of CBDA-4.

SUMMARY

A method of making a cis-cyclobutane-1,2-dicarboxylic acid monomer includes melting trans-cinnamic acid, dissolving trans-cinnamic acid from step a in an organic solvent to form a trans-cinnamic acid solution, mixing the trans-cinnamic acid solution from step b into a poor solvent to create a slurry, and irradiating the slurry from step c with a UV irritation source to photo-dimerize β-trans-cinnamic acid and form cis-cyclobutane-1,2-dicarboxylic acid.

BRIEF DESCRIPTION OF THE DRAWINGS

FIGS. 12A-12E show the X-ray structures of CBDA-4 obtained through single crystal XRD.

FIGS. 17A-16C show NMR spectra of the photodimerization and thermodegradation between trans-cinnamic acid and CBDA-4.

DETAILED DESCRIPTION

Figure 1:
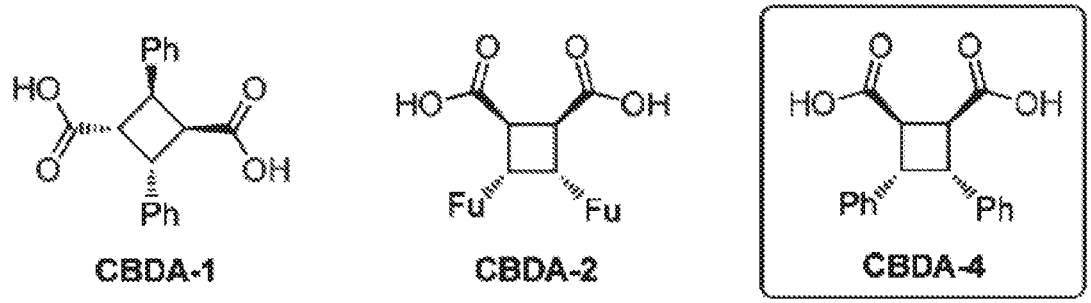
FIG. 1 shows chemical structures of CBDA-1, CBDA-2, and CBDA-4

Recent studies have shown cis-cyclobutane-1,2-dicarboxylic acid (CBDA-4) and its derivatives are suitable for polymer synthesis. CBDA monomers can be derived from readily available starting materials, including bio-based chemicals, that are degradable. Thus, CBDAs can be a green alternative to other polymer building blocks. FIG. 1 shows chemical structures of CBDA-1, CBDA-2, and CBDA-4. Disclosed is a method of reliably producing CBDA-4 monomers in larger quantities than with previous methods.

Figure 2A:
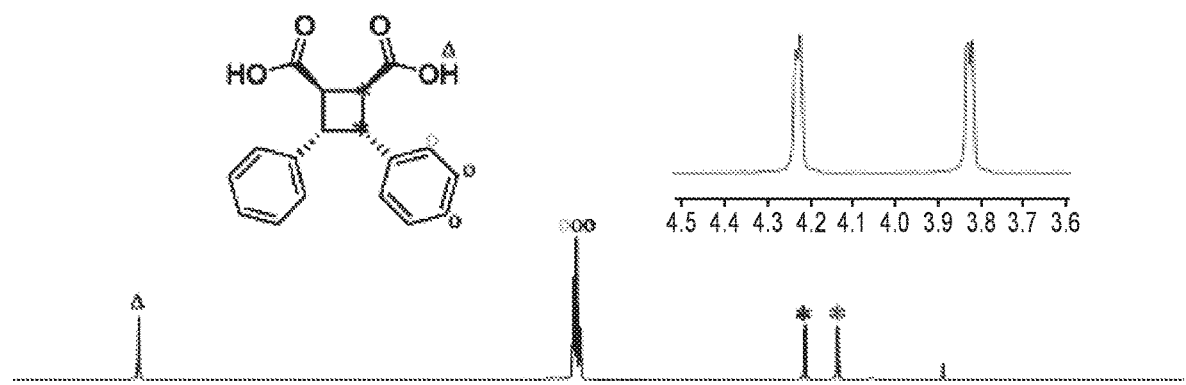
FIGS. 2A-2B compare chemical structures and NMR spectra of CBDA-1 and CBDA-4.
Figure 2B:
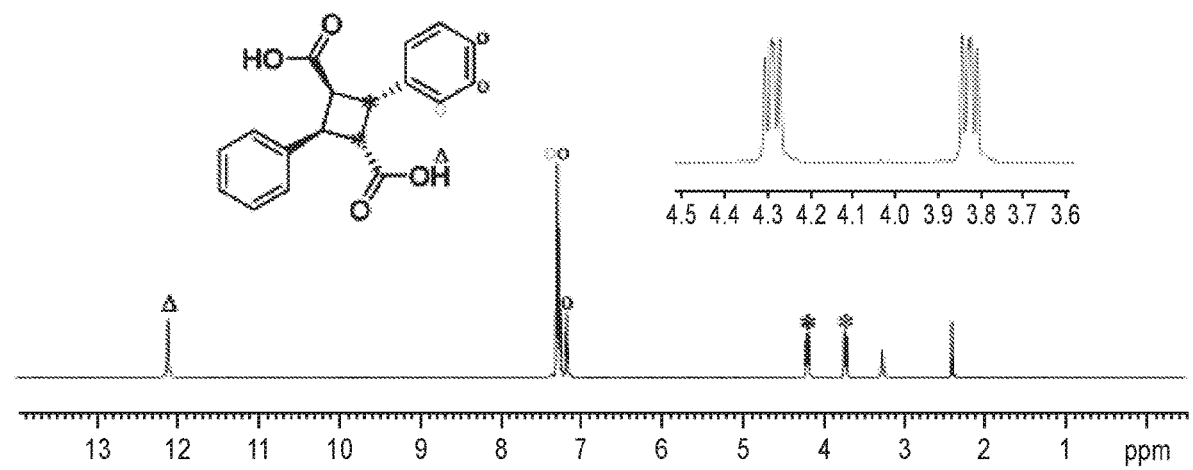

FIGS. 2A-2B compare chemical structures and NMR spectra of CBDA-1 and CBDA-4. FIG. 2A shows the proton NMR spectra of CBDA-4 collected in DMSO-$d_6$, while FIG. 2B shows the proton NMR spectra of CBDA-1 collected in DMSO-$d_6$.

For both CBDA monomers, the NMR spectra show a hydroxyl group at 12.2 ppm. The range from 3.6 to 4.5 ppm is inset into each figure. The inset range shows carbons in the butane ring of each CBDA monomer. Specifically, the spectrum for CBDA-4 shows two new doublets at 4.22 and 3.83 ppm compared to the spectrum of cinnamic acid (shown and discussed with reference to FIGS. 7A-7B). These peaks correspond to the cyclobutane ring in CBDA-4 with mirror symmetry. In contrast, the proton NMR of CBDA-1 shows two doublet-of-doublets peaks around 4.30 and 3.83 ppm, which are consistent with the center symmetry of CBDA-1. The chemical shifts of the phenyl rings on CBDA-1 and CBDA-4 are also different, which can be attributed to the different structural symmetry.

CBDA-4, along with its stereoisomer CBDA-1 can be synthesized from two polymorphs: β-trans-cinnamic acid and α-trans-cinnamic acid, respectively, in their solid state. In their crystalline states, α-trans-cinnamic acid has head-to-tail packing, while β-trans-cinnamic acid has head-to-head packing. However, the metastable crystalline form of β-trans-cinnamic acid readily transforms to the more stable α-trans-cinnamic acid. The low energy barrier between α-trans-cinnamic acid and β-trans-cinnamic acid forms makes reliable production of CBDA-4 challenging. Only photodimerization of the β-trans-cinnamic acid form leads to CBDA-4. In contrast, photodimerization of the α-trans-cinnamic acid leads to CBDA-1 monomers. This has resulted in conflicting experimental results regarding synthesis of CBDA-4 in the prior art.

Previously, CBDA-4 has been synthesized by first converting trans-cinnamic acid to its p-nitrophenyl ester or 1,3-trimethlene diester for photodimerization, and then hydrolyzing the ester dimer back to CBDA-4. This process is time intensive and wasteful, producing only a small amount of CBDA-4. Other methods have used transition-metal-catalyzed enantioselective synthesis of cyclobutane derivates, but in these reactions CBDA-4 is only a minor produce. In lieu of these prior art methods, a simple, reliable, and scalable method of making CBDA-4 is disclosed here.

Figure 3:
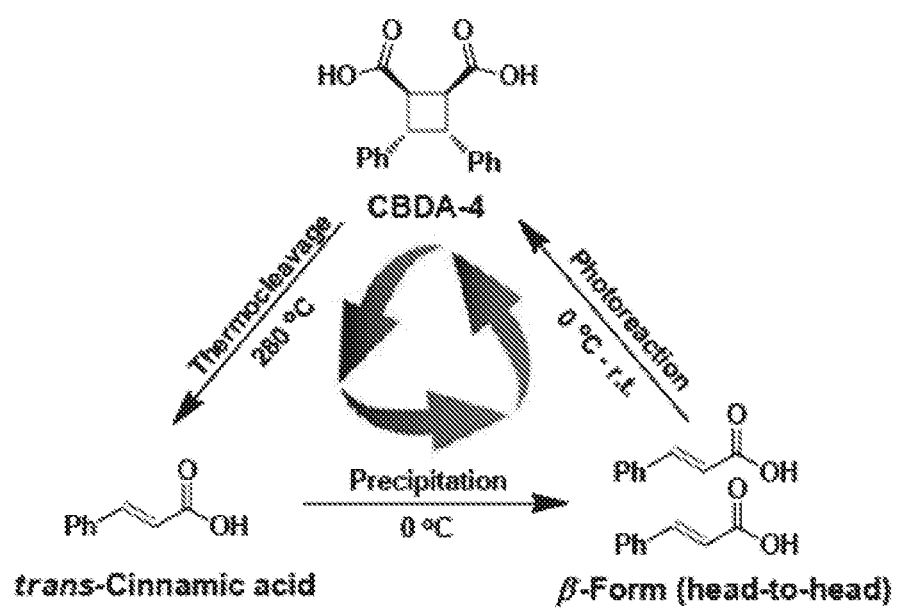
FIG. 3 is a schematic showing a scalable synthesis of CBDA-4, a thermally cleavable di-acid building block. The method includes capturing and photodimerizing a metastable crystalline solid of trans-cinnamic acid.

FIG. 3 is a schematic showing a dependable and scalable synthesis method of CBDA-4, a thermally cleavable di-acid polymer building block, from β-trans-cinnamic acid. The method is a facile process where β-trans-cinnamic acid is maintained in head-to-head packing β form and subsequently irradiated to produce CBDA-4.

First, commercially obtained trans-cinnamic acid is melted (trans-cinnamic acid can be purchased from Alfa Aesar, Acros Organic, Matheson Coleman & Bell Manufacturing Chemists, or other sources). trans-cinnamic acid can be melted, for example, in an oven. The melting point of trans-cinnamic acid, as shown in Table 1, is about 133 degrees Celsius. (The melting points for β-trans-cinnamic acid and α-trans-cinnamic acid were measured on a DigiMelt MPA160—apparatus from Stanford Research Systems at a rate of 2° C./min).

TABLE 1

| Entry | β-trans-cinnamic acid (° C.) | α-trans-cinnamic acid (° C.) |
| --- | --- | --- |
| 1 | 133.1-133.7 | 133.6-134.5 |
| 2 | 133.4-134.3 | 133.4-134.4 |
| 3 | 133.2-134.1 | 133.5-134.2 |
| Average | 133.2-134.0 | 133.5-134.4 |

Thus, commercially obtained trans-cinnamic acid can be melted at about 150° C. for two hours in an oven to fully melt the material. Alternative methods of melting with temperature ranging from 134 to 240° C. can be used, for example, melting at 180° C. for half hour. Skipping the step of melting and heating trans-cinnamic acid can lead to the formation of CBDA-1 instead of CBDA-4.

Next, trans-cinnamic acid is dissolved in an organic solvent to form a trans-cinnamic acid solution. The organic solvent can be, for example, dimethylformamide (DMF), dimethyl sulfoxide (DMSO), diethylformamide (DEF), N-methyl-2-pyrrolidone (NMP), tetrahydrofuran (THF), acetonitrile, and alcohols. The resulting solution can be heated, sonicated, or stirred by other methods to fully dissolve trans-cinnamic acid in the organic solvent. After mixing, the solution should be filtered using techniques known in the art to remove any possible α-trans-cinnamic acid crystal seed.

Subsequently, the trans-cinnamic acid solution is mixed into a poor solvent with temperature near 0° C., for example, ice water. Alternatively, a poor solvent (or mixed poor solvent) with low solubility for trans-cinnamic acid such as brine, hexane, cyclohexane, pentane, heptane, or petroleum ether at a temperature below 15° C. can be used. The trans-cinnamic acid can be mixed into the solvent with stirring to create a slurry. The trans-cinnamic acid solution should be precisely added to the solvent. The trans-cinnamic acid solution can be added to the solvent in a dropwise method or by injection, for example, with a syringe or any other injection device known in the art. The trans-cinnamic acid solution is mixed directly into the solvent. In ice water, this avoids trans-cinnamic acid deposition on top of ice floating in the water, preventing formation of any seeds of the stable α-trans-cinnamic acid form. If seeds of α-trans-cinnamic acid are formed, CBDA-1 is the major product after the photoreaction instead of CBDA-4. The trans-cinnamic acid in β form is precipitated out as a white powder suspended in the ice water. This can be confirmed by powder XRD.

Figure 4:
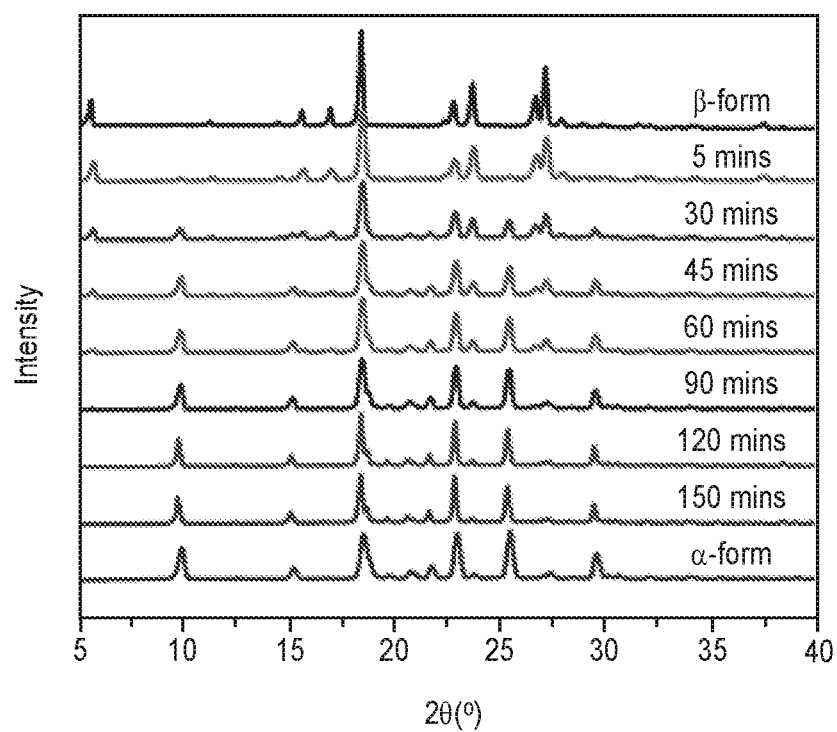
FIGS. 4 and 5 show powder X-ray diffraction (XRD) analysis of trans-cinnamic acid.
Figure 5:
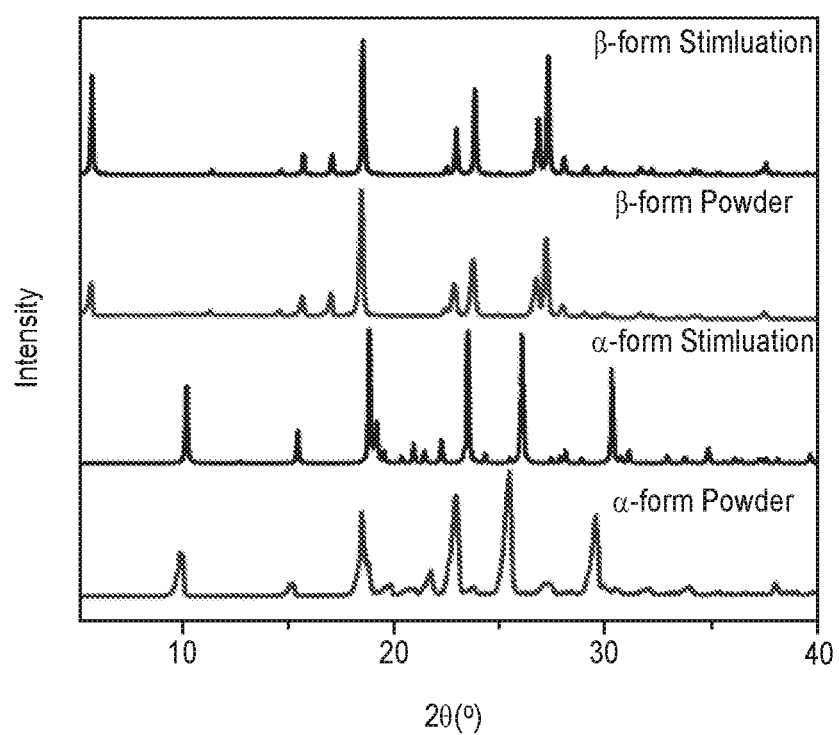
Figure 6:
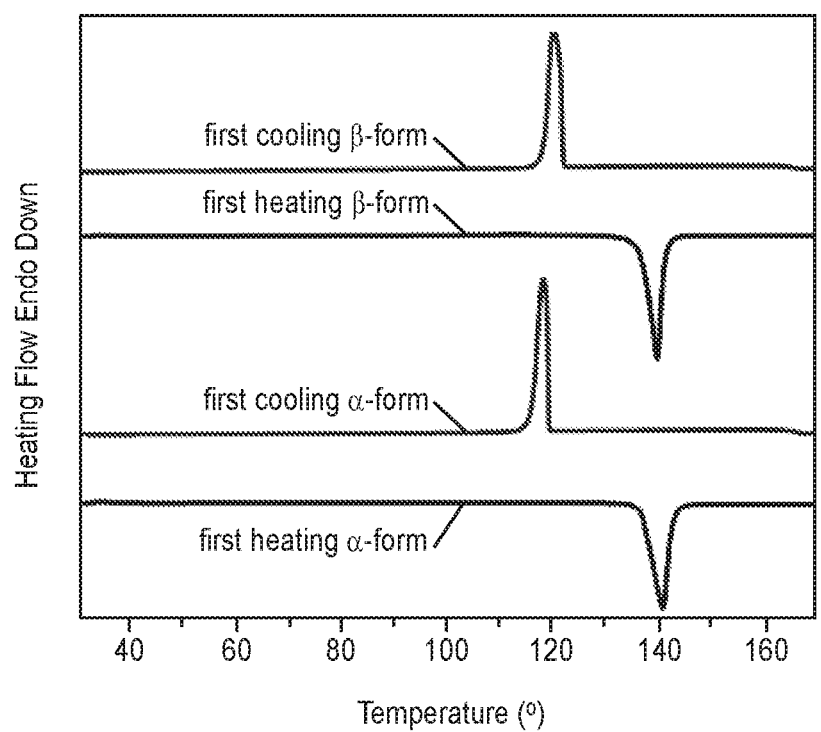
FIG. 6 shows differential scanning calorimetry (DSC) analysis of trans-cinnamic acid.

The phase transformation of β- to α-trans-cinnamic acid was studied by both powder x-ray diffraction (XRD) shown in FIGS. 4, 5 and differential scanning calorimetry (DSC), results shown in FIG. 6. FIG. 4 shows phase transitions of β-trans-cinnamic acid to α-trans-cinnamic acid at 50° C. FIG. 5 shows further powder XRD information on trans-cinnamic acid, confirming the "head-to-head" β-trans-cinnamic acid precipitated in the ice-water solution. Simulation data in FIG. 4 was obtained from X-ray single crystal data of trans-cinnamic acid. As a note, samples of β-trans-cinnamic acid can be converted to α-trans-cinnamic acid if ground for powder XRD analysis due to temperature changes associated with grinding the sample.

The powder pattern of β-trans-cinnamic acid in the ice-water solution shown in FIG. 5 was nearly identical to the simulated pattern generated from single crystal diffraction data shown in FIG. 5. The results shown in FIG. 4 indicate that the β-form steadily converts to the α-form as heated over the course of 2.5 hours. The characteristic peaks of β-trans-cinnamic acid at 5.6°, 15.6°, 16.9°, 23.6°, 26.6°, and 27.0° faded gradually upon heating. Meanwhile, new peaks appeared gradually at 9.8°, 15.1°, 18.5°, 21.8°, 25.4°, and 29.5° that can be attributed to α-trans-cinnamic acid.

Figure 7A:
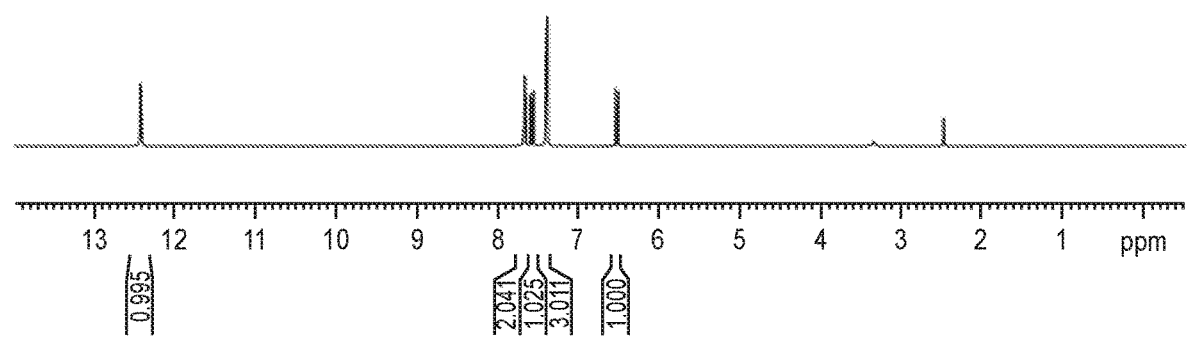
FIGS. 7A-7B show $^1$H and $^{13}$C NMR spectra of trans-cinnamic acid.
Figure 7B:
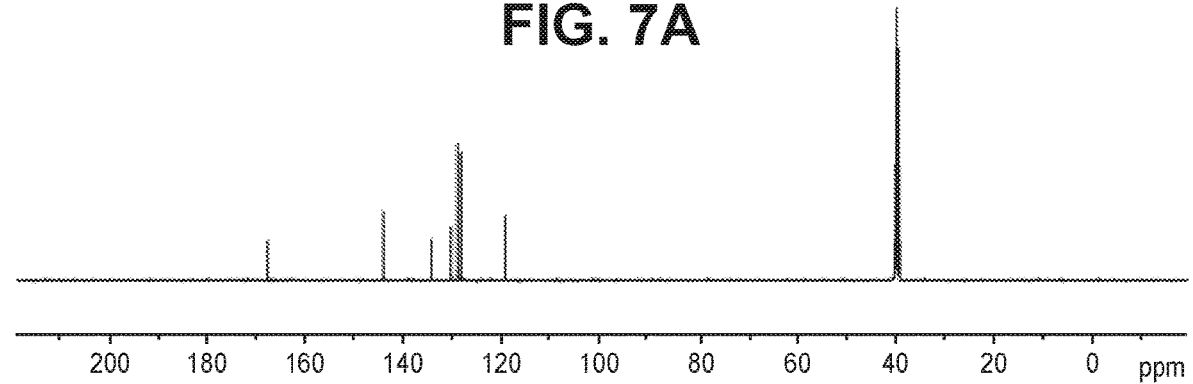
Figure 8A:
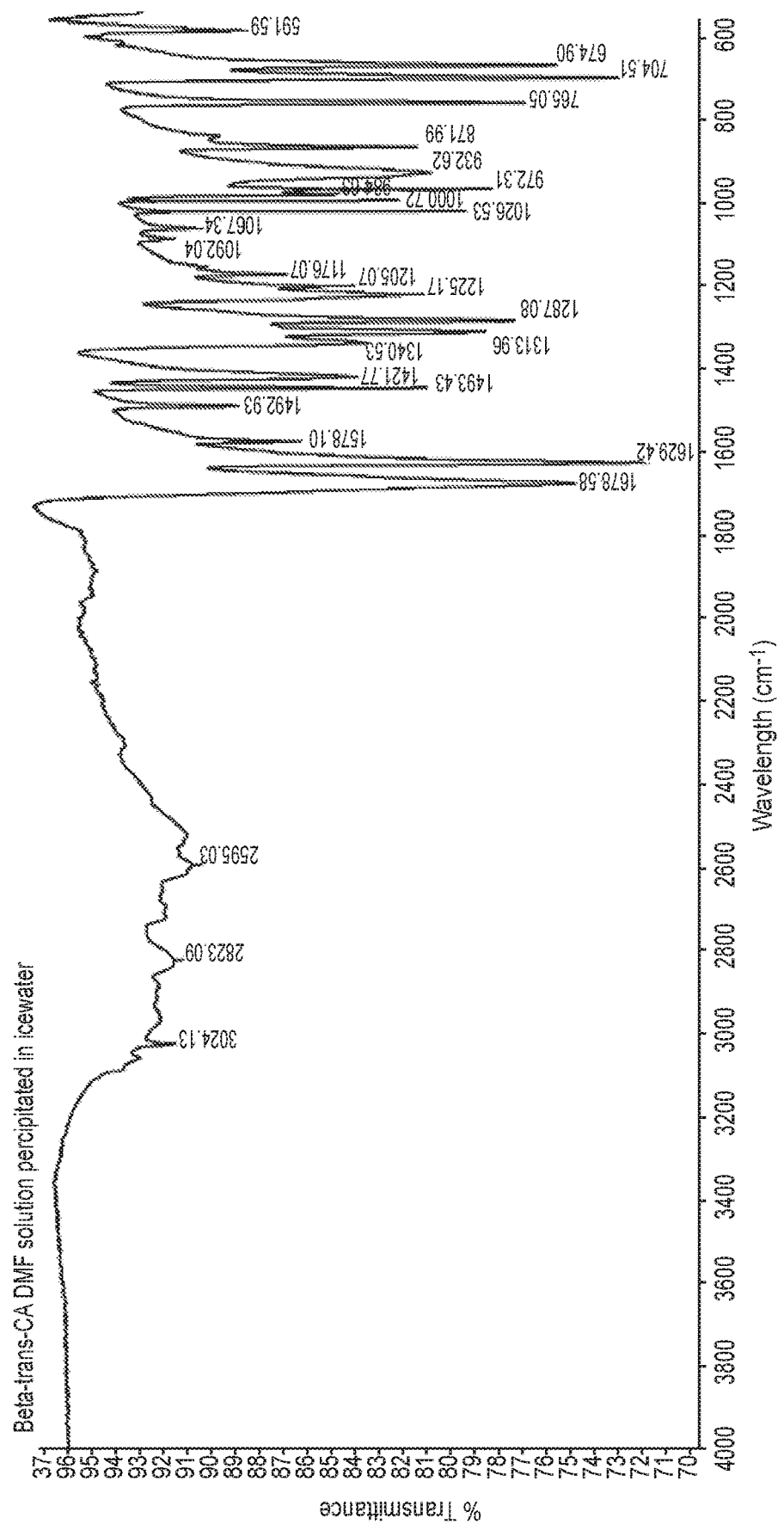
FIGS. 8A-8B shows FT-IR spectra of β- and α-trans-cinnamic acid.
Figure 8B:
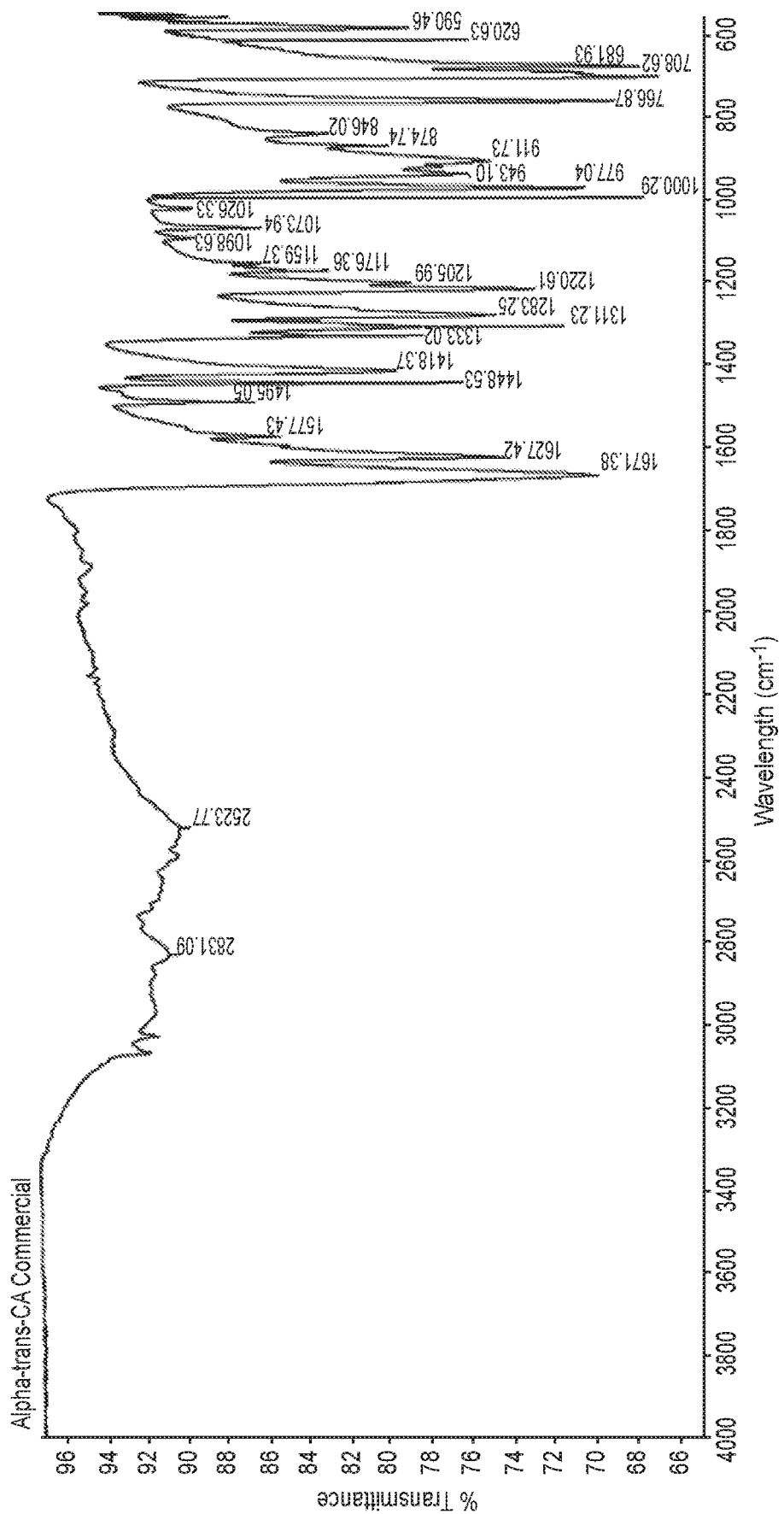

The DSC curves shown in FIG. 6 of both α- and β-forms were recorded from 30° C. to 170° C. with a heating rate of 10° C. per minute under a nitrogen atmosphere. The phase transformation rate from β- to α-trans-cinnamic acid depends on the size of the trans-cinnamic acid crystals. Smaller crystals transform at a quicker rate. The easy transformation of β- to α-trans-cinnamic acid accounts for the similar melting points of β- and α-trans-cinnamic acid between the two polymorphs, and the similar DSC curves pictured in FIG. 6. The XRD results of FIGS. 4, 5, indicated that part of the metastable β-trans-cinnamic acid was converted to the stable α-trans-cinnamic acid during the heating process while the melting points and DSC tests were being conducted.

β- and α-trans-cinnamic acid polymorphs were further studied with proton NMR and FT-IR. FIGS. 7A-7B show $^1$H and $^{13}$C NMR spectra of trans-cinnamic acid, while FIGS. 8A-8B shows FT-IR spectra of β- and α-trans-cinnamic acid, respectively. The spectra pictured in FIGS. 7A-7B and 8A-8B confirm the structure of β- and α-trans-cinnamic acid as shown in FIG. 3.

FIGS. 8A-8B show bands at 1627 cm$^{-1}$, 976 cm$^{-1}$ and 1671 cm$^{-1}$. The 1627 cm$^{-1}$ band indicates a C═C bond stretching. The 976 cm$^{-1}$ bond indicates a C═C—H bond bending out of plane. The 1671 cm$^{-1}$ peak indicates a C═O bond stretching. These peaks are consistent with trans-cinnamic acid. These peaks either disappear or move after photodimerization of the slurry to create CBDA-4.

Figure 9:
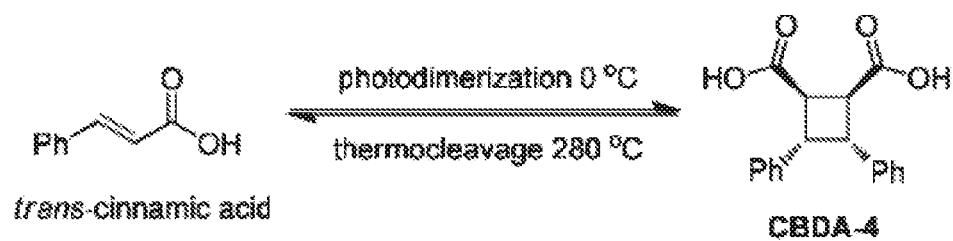
FIG. 9 is a schematic showing the photodimerization and thermodegradation between trans-cinnamic acid and CBDA-4.

If the solvent is ice water, additional ice can be added to the aqueous solution prior to inducement of the photoreaction to produce CBDA-4 to maintain the temperature and prevent formation of α-trans-cinnamic acid seeds. Alternatively, a cooler, such as a low temperature cooling liquid circulator pump chiller cooler, can be used to keep the solvents below 15° C. The slurry is irradiated with blacklight to form cis-cyclobutane-1,2-dicarboxylic acid. FIG. 9 is a schematic showing the photodimerization of trans-cinnamic acid to CBDA-4. In this schematic, head-to-head packed, β-trans-cinnamic acid is photodimerized to CBDA-4.

Figure 10:
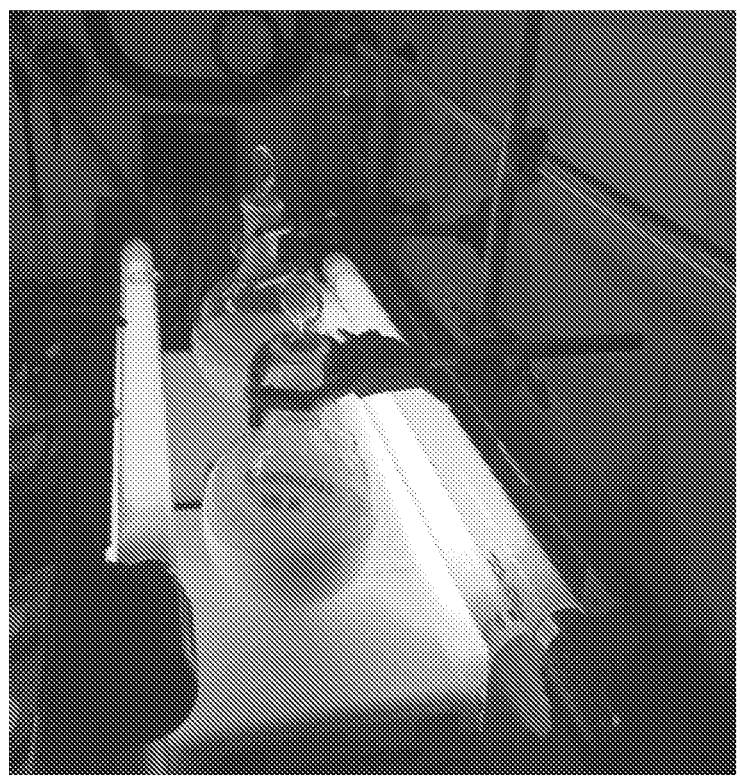
FIG. 10 is an image of the irradiation step producing CBDA-4.

(CBDA-4). FIG. 10 is an image of the irradiation step as performed on a laboratory scale. A person skilled in the art will know that equivalent techniques can be used to scale to the process to pilot, semi-works, and industrial scales. In FIG. 10, round bottoms flasks of the slurry 10 are held by clamps near the irradiation source. In this step, the photoreaction can be started at 0° C. when the β-trans-cinnamic acid has precipitated from the ice water. Once the ice has melted, the slurry can be allowed to gradually warm to room temperature throughout the photoreaction without harmful effect. Irradiation is continued with the blacklight source until dimerization is complete.

The irradiation source can be a residential blacklight such as an ECO-UV irradiation source. For example, EIKO 15526 F15T8 with a BL Fluorescent Blacklight Bulb 365 nm can be used. Other UV irritation source such as germicidal lamp, LED (Light-emitting diode), floodlight, mercury vapor lamp, and sunlight can alternatively be used for the photoreaction. The irradiation source should be kept as close as is reasonable to the slurry for efficient irradiation. Flasks for slurry can be normal laboratory glassware, such as round-bottom flasks, Erlenmeyer flasks, or beakers, as about 90% of blacklight irradiation will permeate the glass. A person skilled in the art will know that equivalent techniques can be used to scale to the process to pilot, semi-works, and industrial scales.

Figure 11A:
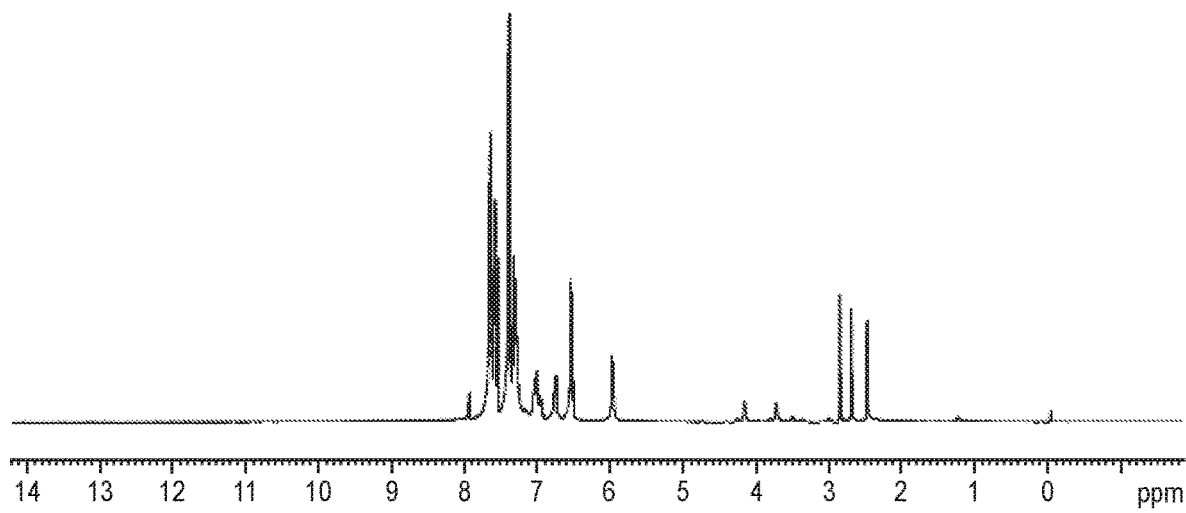
FIGS. 11A-11B are NMR spectra of the filtrate after the irradiation step.
Figure 11B:
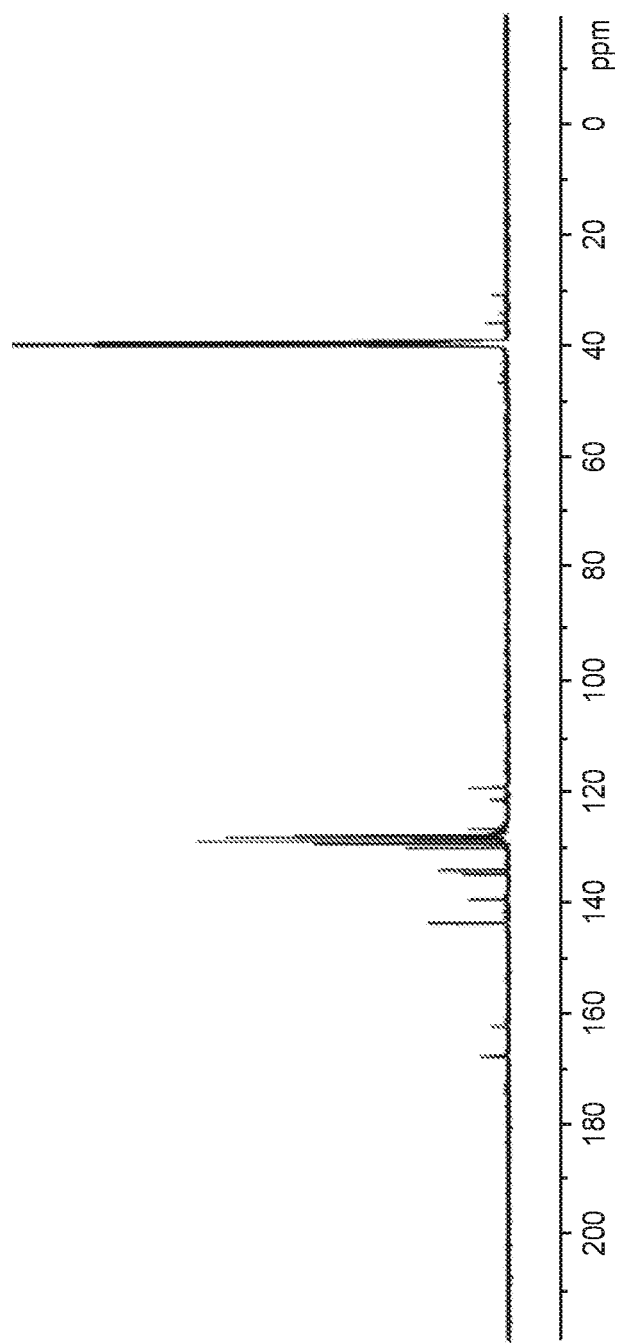

CBDA-4 is then precipitated and filtered out. FIGS. 11A-11B are NMR spectra of the filtrate. FIG. 11A is a proton $^1$H NMR spectrum of the residue from the filtrate of the CBDA-4 photoreaction. FIG. 11B is a $^{13}$C NMR spectrum of the same filtrate. The peaks on both $^1$H and $^{13}$C spectra indicate the filtrate contains small amounts of trans-cinnamic acid, cis-cinnamic acid, DMF solvent, and CBDA-4. This filtrate can be dissolved in an organic solvent, such as acetonitrile with acetic acid, sonicated, and allowed to re-crystalize as high quality CBDA-4 colorless plates.

The resulting CBDA-4 mixture can be cleaned with ethanol (or other appropriate solvent) to produce CBDA-4, a white powder, confirmed by the data discussed in depth with references to FIGS. 12-16 below. Specifically, the complete dimerization of trans-cinnamic acid to CBDA-4 is show in the single-crystal XRD data of FIGS. 12A-12C, the NMR, FT-IR, and UV-Vis spectra of FIGS. 13-15, and the DSC curves of FIGS. 16A-16B.

FIGS. 12A-12E show the X-ray structures of CBDA-4 obtained through single-crystal XRD. For XRD analysis, plate-shaped single crystals of CBDA-4 were obtained in acetonitrile solution containing a small amount of acetic acid at room temperature. The X-ray structures of CBDA-4 in FIGS. 12A-12D represent 50% electron density. Hydrogens are omitted for clarity.

FIG. 12A shows the crystal structure of CBDA-4. FIG. 12B shows the cyclobutane-1,2-diacid moiety in CBDA-4 with inner angle 87°-88°. FIG. 12C shows the cyclobutane-1,2-diacid moiety adopting a 20° puckered conformation. Phenyl groups are omitted for clarity. FIG. 12D shows a front view and side view of a supramolecular helix of CBDA-4 via hydrogen bonds. Phenyl groups are omitted for clarity.

The views of FIGS. 12A-12D confirm the orientation of the adjacent 1,2-dicaroboxylic groups on the cyclobutane ring, showing its structural similarity to o-phthalic acid and its potential to serve as a diacid building block in polymer materials.

The cyclobutane ring in CBDA-4 adopts a 20° puckered conformation in the solid state (see FIG. 12C). This is different from the planar conformation of the cyclobutane ring in CBDA-1 structures. The angles in the CBDA-4 cyclobutane ring are 87.82(9), 88.21(9), 87.68(9), and 88.80 (9)°, which indicate the ring strain in the CBDA-4 structure.

Additionally, shown in FIG. 12D, a supramolecular helix of CBDA-4 self-assembles along the b axis cia the intermolecular hydrogen bonds between carboxylic acid groups (The $O_{C═O}\ldots O_{OH}$ hydrogen bonds are 2.680(2)-2.694(2) Å in FIG. 12D). This indicates that CBDA-4 could be used to prepare supramolecular materials such as metal-organic frameworks or hydrogen-bonded organic frameworks. These hydrogen bonds also effect the melting point of CBDA-4, which ranges from 207.6-208.6° C.

Figure 12E:
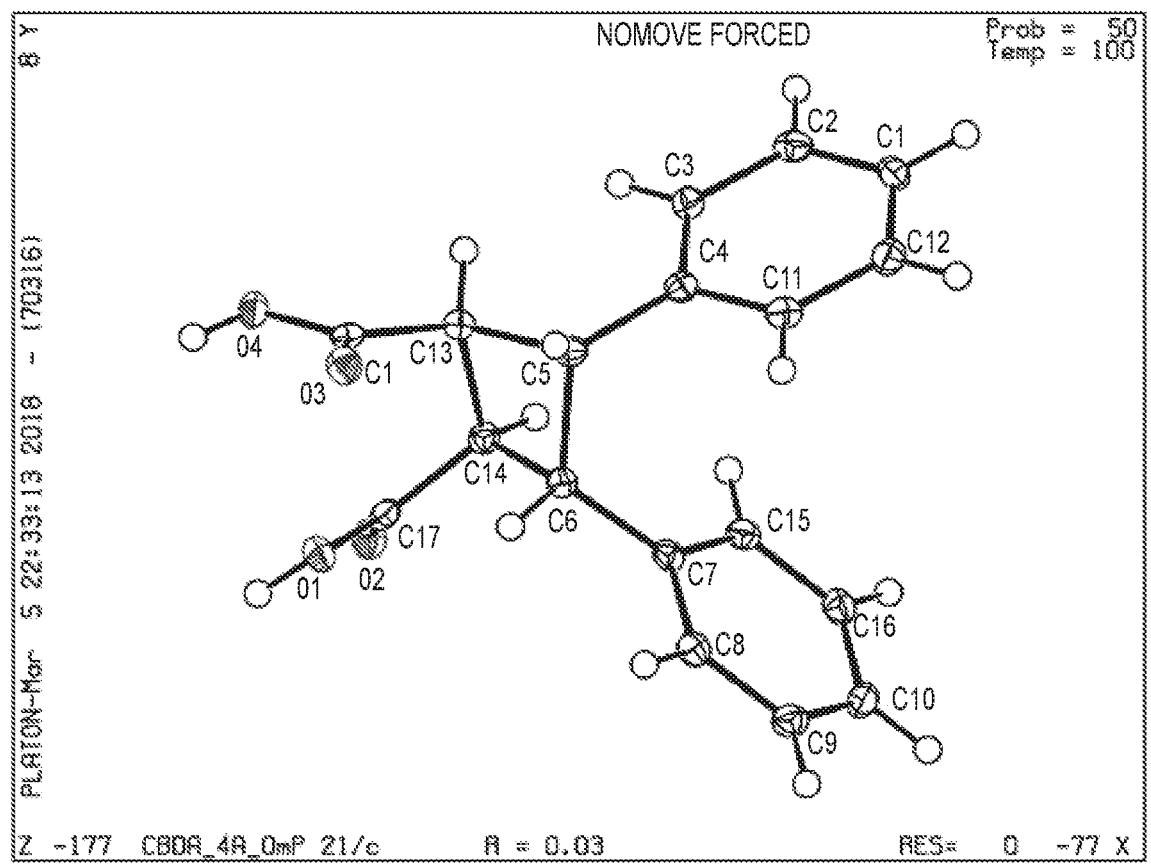

FIG. 12E shows crystal data of CBDA-4. Further information from CBDA-4 crystal data is summarized below in Table 2.

TABLE 2

| Crystal | CBDA-4 |
| --- | --- |
| CCDC # | 1857653 |
| Formula | $C_{18}H_{16}O_4$ |
| FW | 296.31 |
| Crystal size [mm] | 0.600 × 0.450 × 0.300 |
| Crystal system | Monoclinic |
| Space group | $P2_1/c$ |
| a (Å) | 16.2829(11) |
| b (Å) | 5.5494(3) |
| c (Å) | 16.4604(10) |
| α (°) | 90 |
| β (°) | 113.418(4) |
| γ (°) | 90 |
| V (Å$^3$) | 1364.85(15) |
| Temp. (K) | 100(2) |
| Z | 4 |
| pcalc (g · cm$^{-3}$) | 1.442 |
| μ (mm$^{-1}$) | 0.102 |
| Radiation type | MoKα (λ = 0.71073) |
| F(000) | 624 |
| Reflections collected | 10087 |
| Independent reflections | 2451 |
| R1/wR2 (I ≥ 2σ) (%) | 3.30/12.84 |
| R1/wR2 (all data) (%) | 3.62/13.95 |

Figure 13A:
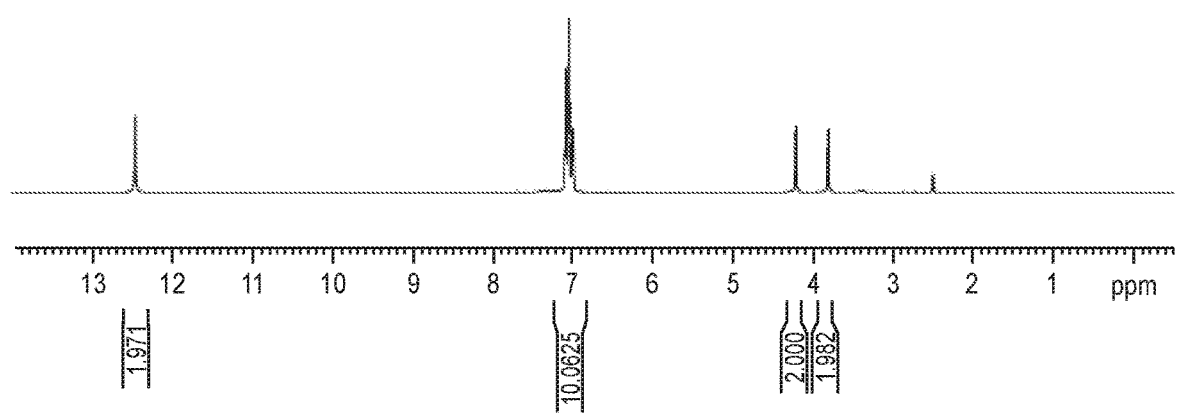
FIGS. 13A-13E show NMR spectra of CBDA-4 produced according to the disclosed method.
Figure 13B:
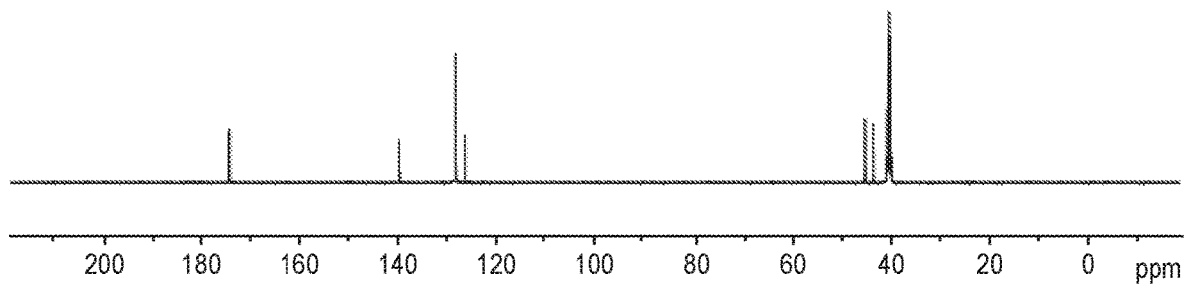
Figure 13C:
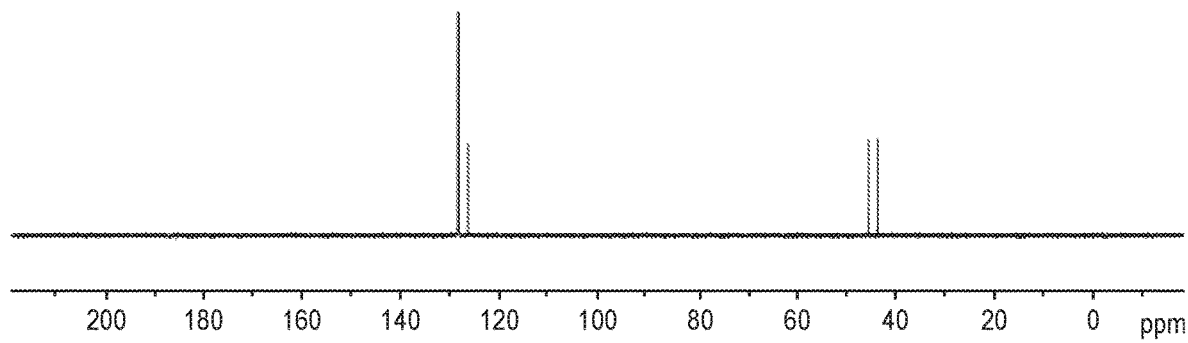
Figure 13D:
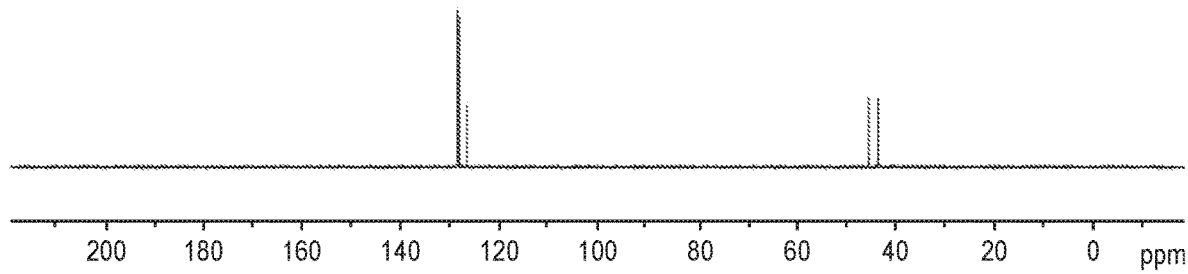
Figure 13E:
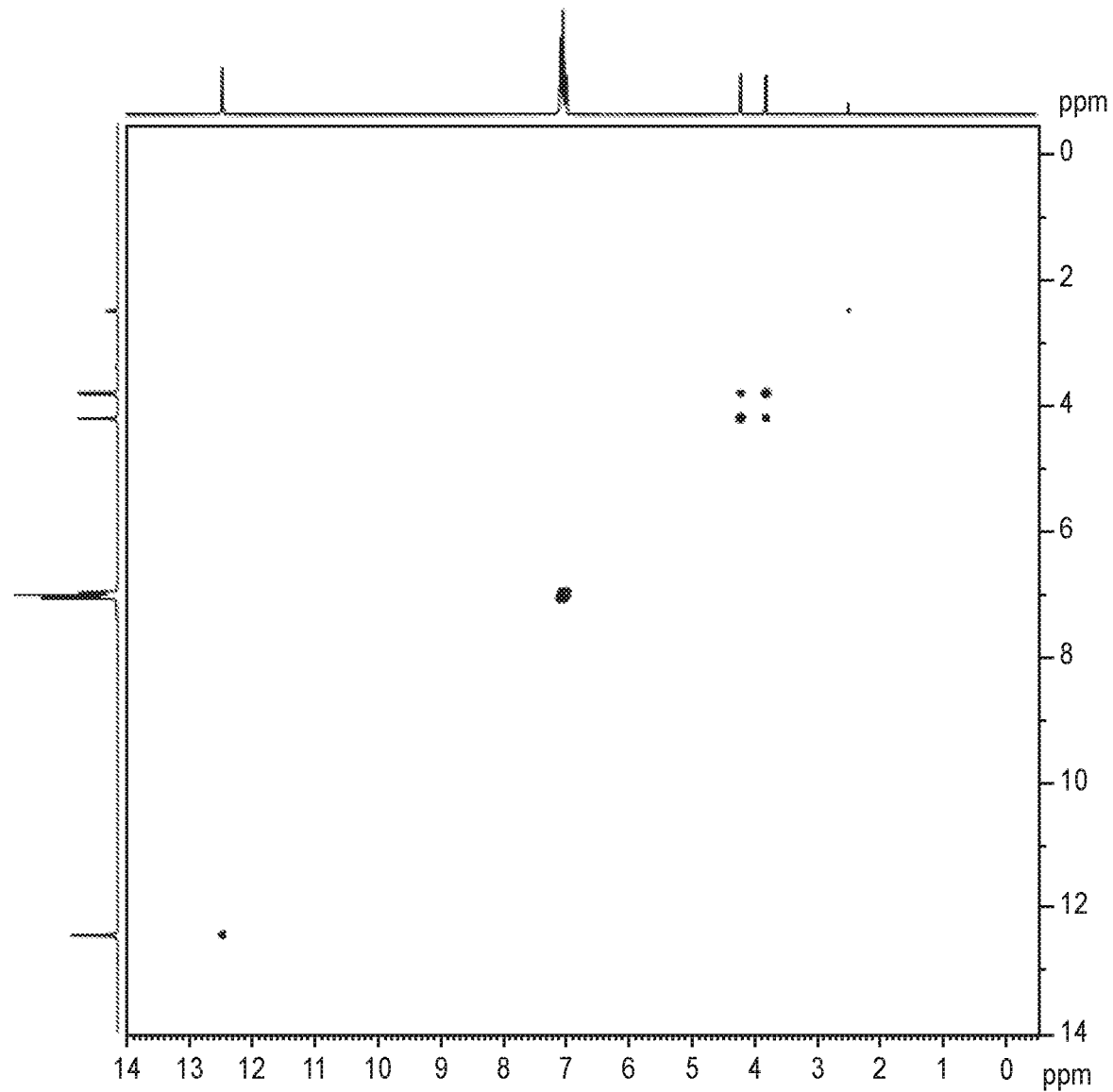

FIGS. 13A-13E show NMR spectra of CBDA-4 produced by the disclosed method. The method described in reference to FIG. 3 produces CBDA-4. FIG. 13A shows the $^1$H NMR spectrum of CBDA-4. FIG. 13B shows the $^{13}$C NMR spectrum of CBDA-4. FIG. 13C shows the DEPT135 NMR spectrum of CBDA-4. FIG. 13D shows the DEPT90 NMR spectrum of CBDA-4. FIG. 13E shows the COSY NMR spectrum of CBDA-4. All NMR samples were prepared in DMSO-$d_6$.

In the $^1$H NMR spectrum of CBDA-4 (FIG. 13A), two new doublets at 4.22 and 3.82 ppm appeared compared with the $^1$H NMR spectrum of trans-cinnamic acid (see FIGS. 7A-7B). These peaks correspond to the cyclobutane ring in CBDA-4 with mirror symmetry (see FIG. 1).

CBDA-4 produced by the disclosed method samples were further treated with sodium hydroxide or hydrogen chloride to study the effect of acid and base on the CBDA-4 cyclobutane ring. In both cases, the produced NMR spectra ($^1$H and $^{13}$C) were the same as the spectra produced from study of the original CBDA-4 product, indicating the cyclobutane ring is stable under acid or base conditions.

Figure 14:
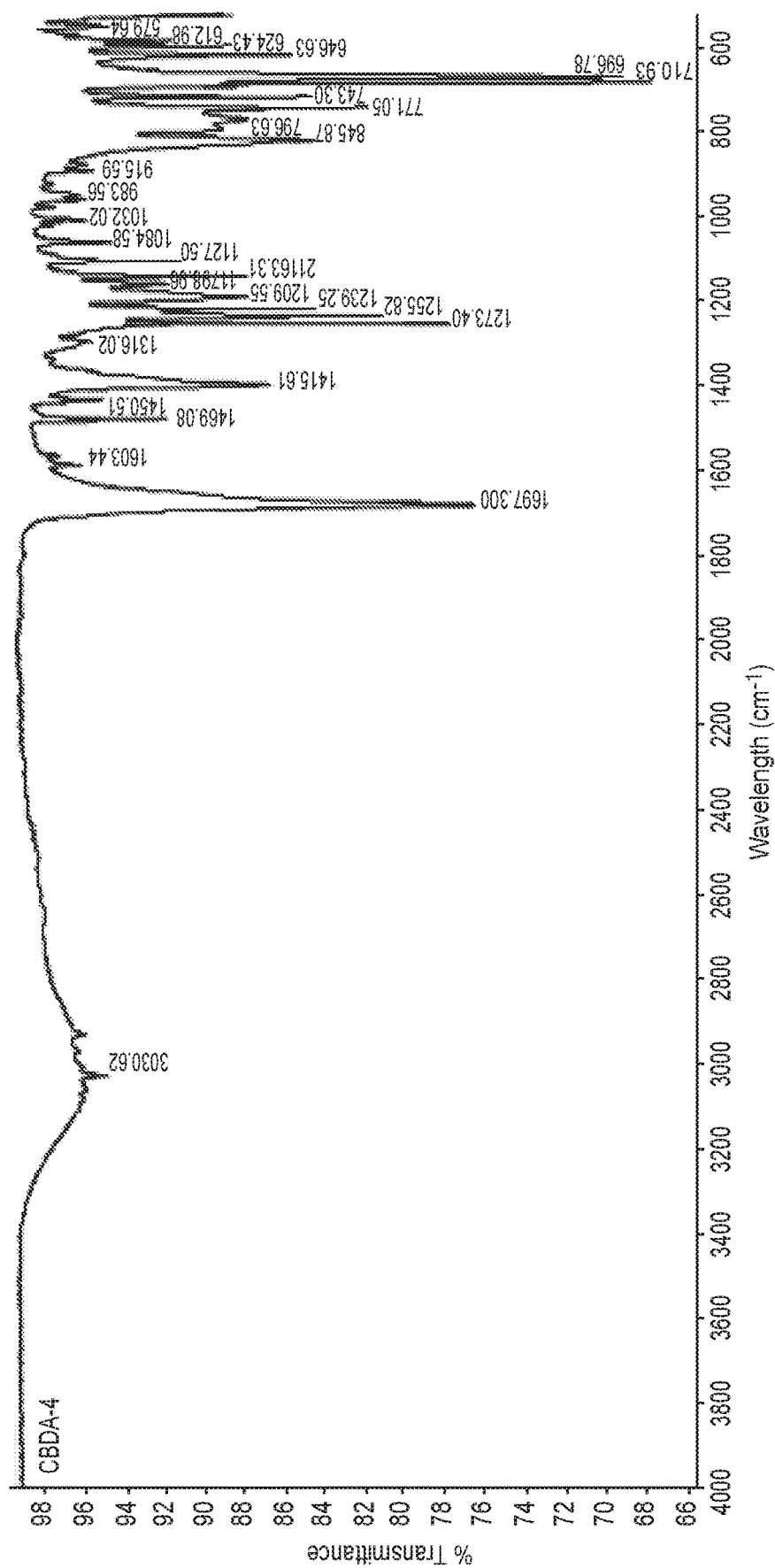
FIG. 14 shows an PT-IR spectrum of CBDA-4 produced according to the disclosed method.
Figure 15:
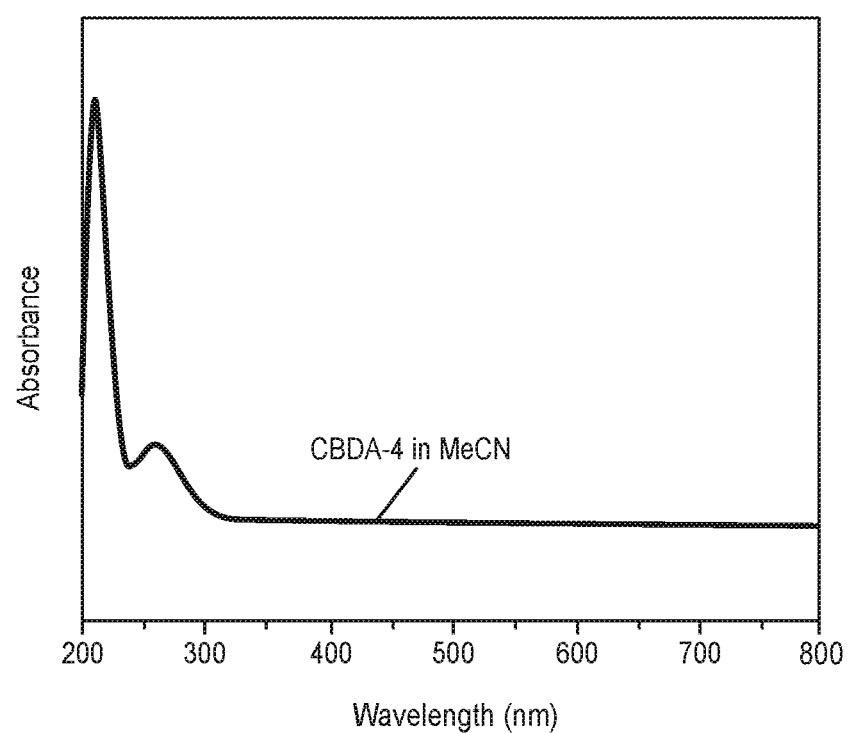
FIG. 15 shows a UV-Vis spectrum of CBDA-4 produced according to the disclosed method.

FIG. 14 shows an FT-IR spectrum of CBDA-4 produced by the disclosed method, and FIG. 15 shows a UV-Vis spectrum of CBDA-4 produced by the disclosed method where the maximum absorbance of CBDA-4 was at 210 nm. Compared to trans-cinnamic acid with a maximum absorbance at 274 nm, CBDA-4 has an ultraviolet absorbance at shorter wavelength. The completion of dimerization of trans-cinnamic acid to CBDA-4 is indicated in the FT-IR spectrum by the disappearance of the bands at 1627 cm$^{-1}$ (indicating C=C stretching) and at 976 cm$^{-1}$ (indicating out of plane bending of C=C—H). The formation of CBDA-4 was further confirmed by shifting of the band at 1671 cm$^{-1}$ (indicating C=O stretching) to 1697 cm$^{-1}$.

Figure 16A:
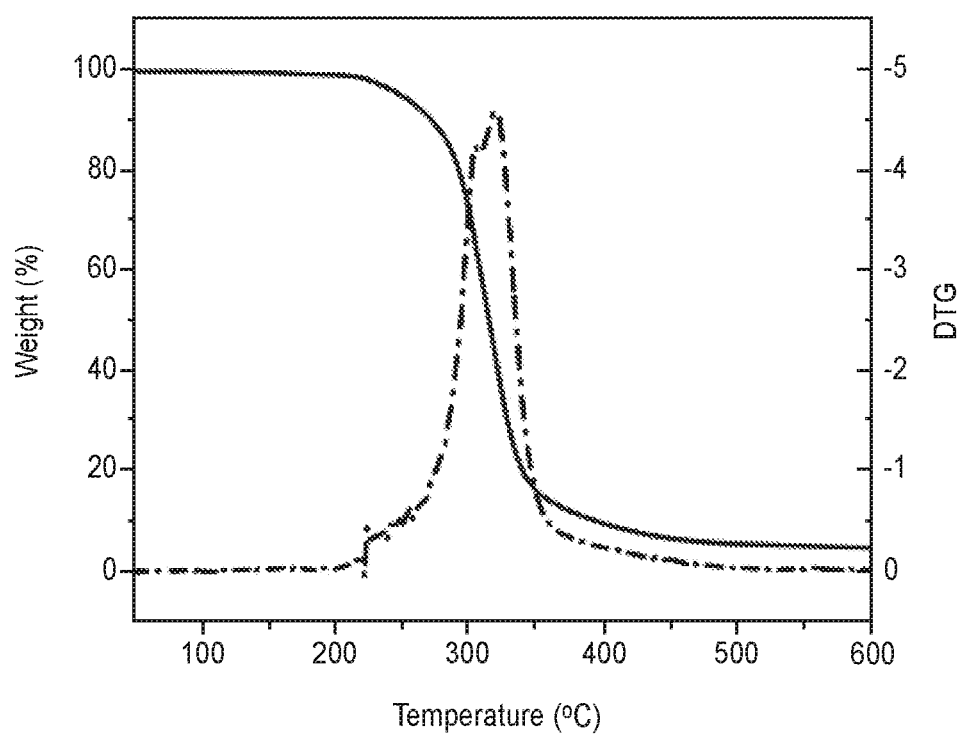
FIGS. 16A-16C show the thermostability of CBDA-4 produced according to the disclosed method over a range of temperatures.
Figure 16B:
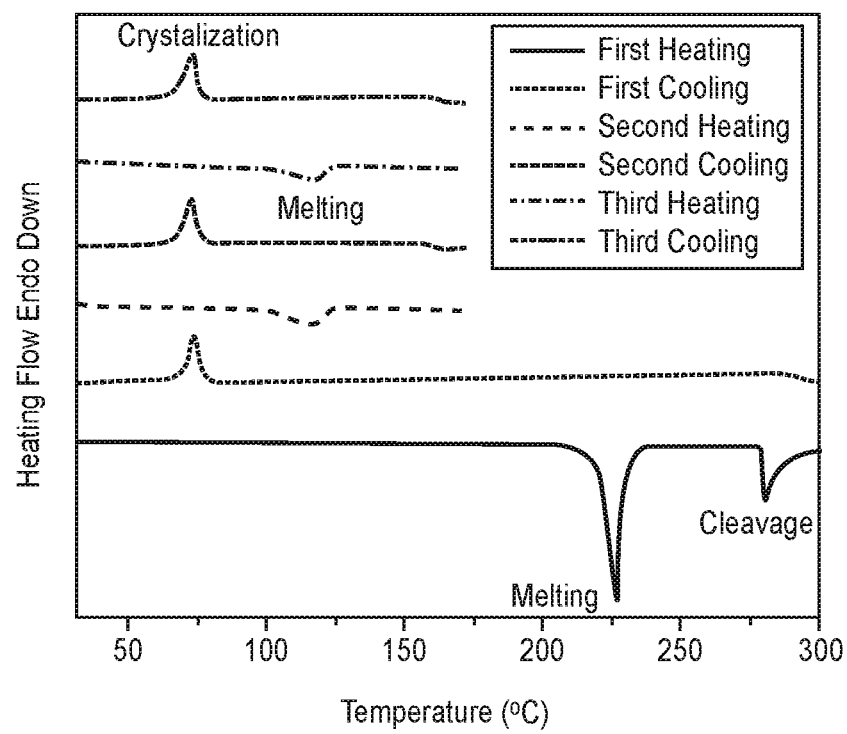
Figure 16C:
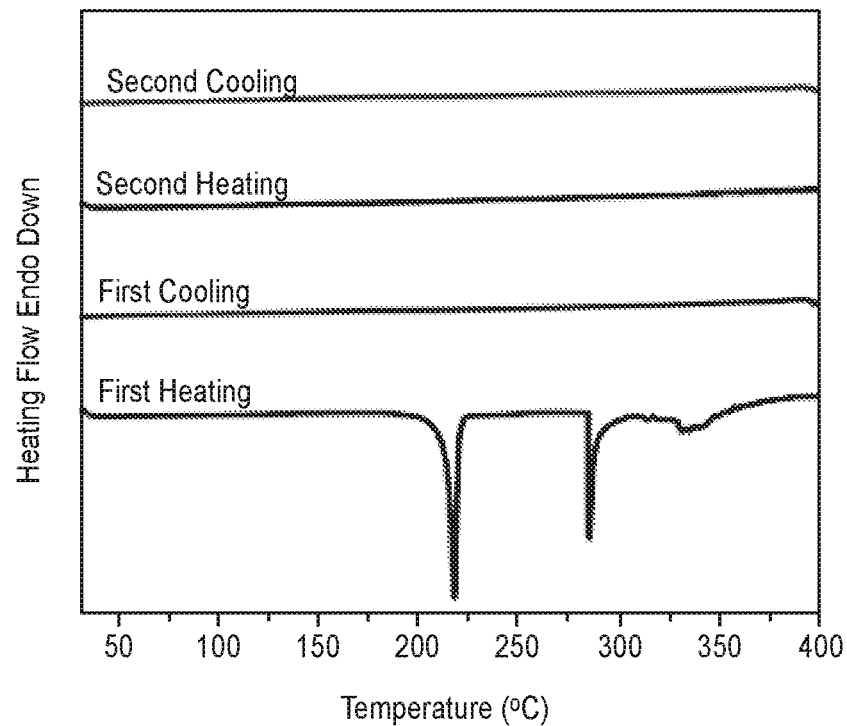

FIGS. 16A-16C show the thermostability of CBDA-4 produced by the disclosed method over a range of temperatures. FIG. 16A is a thermogravimetric analysis (TGA) of CBDA-4 from 50° C. to 600° C. with a heating rate of 20° C. per minute under nitrogen atmosphere. FIGS. 16B-16C show differential scanning calorimetry (DSC) analyses. FIG. 16B shows DSC recorded from 30° C. to 300° C. for the first heating cycle and 30° C. to 170° C. for the second and third heating cycles with a heating rate of 20° C. per minute. FIG. 16C shows DSC recorded from 50° C. to 400° C. with a heating rate of 10° C. per minute. Both were recorded under nitrogen atmosphere.

TGA in FIG. 16A shows no obvious weight loss below 200° C. and 5% weight loss around 250° C. The residual weight at 600° C. was 4%. The derivation exhibited the temperature of maximum weight loss for CBDA-4 as 319° C.

DSC in FIGS. 16B and 16C showed no change observed below the melting point of CBDA-4 around 208° C. DSC further shows a second endothermic peak around 280° C. In DSC testing, the CBDA-4 sample was heated to 300° C. for five minute and subsequently cooled down to 30° C. When the sample was heated for a second time, a new endothermic peal appeared around the melting point of trans-cinnamic acid. This suggests thermal cleavage of CBDA-4 at high temperatures.

Both TGA and DSC analysis indicate that CBDA-4 is stable at temperatures of at least 200° C., meaning CBDA-4 is thermally stable for many applications. Despite the ring strain of the cyclobutane ring, CBDA-4 is reasonably stable. This is due to the [2+2] photocylization (and corresponding reverse reaction) being generally thermally forbidden. In other words, a high thermal energy barrier has to be overcome to break the four-membered ring once it is formed by photoreaction.

Figure 17A:
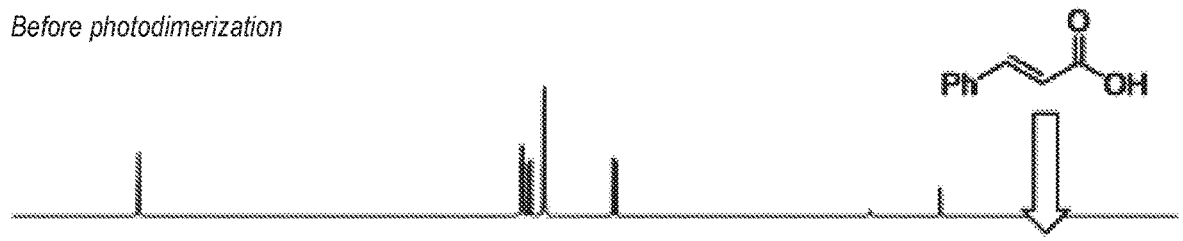
Figure 17B:
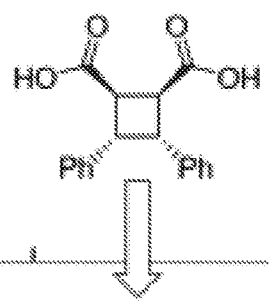
Figure 17C:
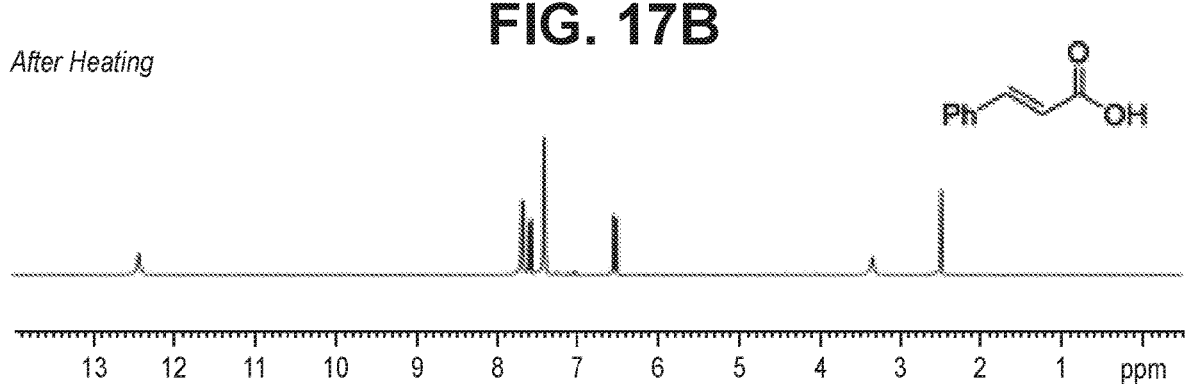

FIGS. 17A, 17B, and 17C show proton NMR of trans-cinnamic acid before photodimerization, CBDA-4 after photodimerization, and resulting trans-cinnamic acid after heating CBDA-4, respectively. Proton NMR analysis was performed in DMSO-$d_6$. The proton NMR spectra of trans-cinnamic acid before photodimerization and CBDA-4 after photodimerization are discussed in depth with reference to FIGS. 7A and 13A, respectively.

FIG. 17C shows a proton NMR that was identical to that of trans-cinnamic acid before photodimerization. To determine what happens to CBDA-4 at the 280° C. mark (a point of interest in the thermostability analysis discussed with reference to FIGS. 16A-16C), a sample of CBDA-4 was heated at 300° C. for 15 minutes under argon. During this process, colorless crystals were formed. In the NMR spectrum of these crystals (FIG. 17C), peaks around 4.22 and 3.83 ppm disappeared, while two new doublet peaks appeared at 7.58 and 6.52 ppm. This indicates double bond formation. This NMR spectrum was identical to that of trans-cinnamic acid (FIG. 17A).

This result indicates that photocycloaddition of trans-cinnamic acid to form CBDA-4 can be reversed by thermocleavage (see also FIG. 9).

Overall, the method disclose with reference to FIG. 3 reliably produces CBDA-4 monomers, as shown in FIGS. 12-16. The produce CBDA-4 monomers are generally stable and additionally thermally cleavable, making them suitable for polymer formation.

Discussion of Possible Embodiments

A method of making a cis-cyclobutane-1,2-dicarboxylic acid monomer includes melting trans-cinnamic acid, dissolving trans-cinnamic acid from step a in an organic solvent to form a trans-cinnamic acid solution, mixing the trans-cinnamic acid solution from step b into a poor solvent to create a slurry, and irradiating the slurry from step c with a UV irritation source to photo-dimerize β-trans-cinnamic acid and form cis-cyclobutane-1,2-dicarboxylic acid.

The method of the preceding paragraph can optionally include, additionally and/or alternatively, any one or more of the following features, configurations and/or additional components:

Melting is done between 134 and 240 degrees Celsius in step a.

The organic solvent is selected from the group consisting of dimethylformamide, dimethyl sulfoxide, diethylformamide, N-methyl-2-pyrrolidone, tetrahydrofuran, acetonitrile, and alcohols in step b.

Dissolving trans-cinnamic acid in the organic solvent comprises heating the trans-cinnamic acid in the organic solvent.

Dissolving trans-cinnamic acid in the organic solvent comprises sonicating the trans-cinnamic acid in the organic solvent.

The method includes filtering the trans-cinnamic acid solution between steps b and c to avoid formation of α-trans-cinnamic acid.

The poor solvent is selected from the group consisting of ice water, brine, hexane, cyclohexane, pentane, heptane, and petroleum ether.

The poor solvent has a temperature lower than 15 degrees Celsius.

Mixing the trans-cinnamic acid solution into the poor solvent in step c comprises adding the solution dropwise to the ice water and stirring.

Mixing the trans-cinnamic acid solution into the poor solvent in step c comprises adding the solution directly to the poor solvent.

Mixing the trans-cinnamic acid solution into the poor solvent comprises injection with an injection device or a dropping device.

Mixing the trans-cinnamic acid solution into the poor solvent avoids formation of α-trans-cinnamic acid.

The method includes further comprising precipitating the β-trans-cinnamic acid in crystal form as part of step c.

Irradiating the slurry as part of step d comprises applying a UV irritation source.

Irradiating the slurry as part of step d is done for at least 15 minutes.

The UV irritation source is selected from the group consisting of blacklight, germicidal lamp, floodlight, mercury vapor lamp, LED, and sunlight.

The method includes cleaning the cis-cyclobutrane-1,2-dicarboxylic acid.

The trans-cinnamic acid has head-to-head packing.

The cis-cyclobutrane-1,2-dicarboxylic acid is recovered as trans-cinnamic acid after heating above 250 degree Celsius.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of making a cis-cyclobutane-1,2-dicarboxylic acid monomer comprises:
   a. melting trans-cinnamic acid;
   b. dissolving trans-cinnamic acid from step a in an organic solvent to form a trans-cinnamic acid solution;
   c. mixing the trans-cinnamic acid solution from step b into a poor solvent to create a slurry; and
   d. irradiating the slurry from step c with a UV irritation source to photo-dimerize β-trans-cinnamic acid and form cis-cyclobutane-1,2-dicarboxylic acid.

2. The method of claim 1, wherein melting is done between 134 and 240 degrees Celsius in step a.

3. The method of claim 1, wherein the organic solvent is selected from the group consisting of dimethylformamide, dimethyl sulfoxide, diethylformamide, N-methyl-2-pyrrolidone tetrahydrofuran, acetonitrile, and alcohols in step b.

4. The method of claim 1, wherein dissolving trans-cinnamic acid in the organic solvent comprises heating the trans-cinnamic acid in the organic solvent.

5. The method of claim 1, wherein dissolving trans-cinnamic acid in the organic solvent comprises sonicating the trans-cinnamic acid in the organic solvent.

6. The method of claim 1, further comprising filtering the trans-cinnamic acid solution between steps b and c to avoid formation of α-trans-cinnamic acid.

7. The method of claim 1, wherein the poor solvent is selected from the group consisting of ice water, brine, hexane, cyclohexane, pentane, heptane, and petroleum ether.

8. The method of claim 1, wherein the poor solvent has a temperature lower than 15 degrees Celsius.

9. The method of claim 1, wherein mixing the trans-cinnamic acid solution into the poor solvent in step c comprises adding the solution dropwise to the ice water and stirring.

10. The method of claim 1, wherein mixing the trans-cinnamic acid solution into the poor solvent in step c comprises adding the solution directly to the poor solvent.

11. The method of claim 1, wherein mixing the trans-cinnamic acid solution into the poor solvent comprises injection with an injection device or a dropping device.

12. The method of claim 1, wherein mixing the trans-cinnamic acid solution into the poor solvent avoids formation of α-trans-cinnamic acid.

13. The method of claim 1, further comprising precipitating the β-trans-cinnamic acid in crystal form as part of step c.

14. The method of claim 1, wherein irradiating the slurry as part of step d comprises applying a UV irritation source.

15. The method of claim 1, irradiating the slurry as part of step d is done for at least 15 minutes.

16. The method of claim 14, wherein the UV irritation source is selected from the group consisting of blacklight, germicidal lamp, floodlight, mercury vapor lamp, LED, and sunlight.

17. The method of claim 1, further comprising cleaning the cis-cyclobutrane-1,2-dicarboxylic acid.

18. The method of claim 1, wherein the trans-cinnamic acid has head-to-head packing.

19. The method of claim 1, wherein the cis-cyclobutrane-1,2-dicarboxylic acid is recovered as trans-cinnamic acid after heating above 250 degree Celsius.

* * * * *